United States Patent
Giftakis et al.

(10) Patent No.: US 7,421,297 B2
(45) Date of Patent: Sep. 2, 2008

(54) MONOPOLAR STIMULATION ASSEMBLY INCLUDING AT LEAST ONE REMOTE ELECTRODE

(75) Inventors: Jonathon E. Giftakis, Maple Grove, MN (US); Jonathan C. Werder, Corcoran, MN (US); Paul H. Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 245 days.

(21) Appl. No.: 11/095,306

(22) Filed: Mar. 31, 2005

(65) Prior Publication Data

US 2006/0229686 A1 Oct. 12, 2006

(51) Int. Cl.
*A61N 1/372* (2006.01)
(52) U.S. Cl. .................................................. 607/45
(58) Field of Classification Search .................. 607/45
See application file for complete search history.

(56) References Cited

U.S. PATENT DOCUMENTS

| | | | |
|---|---|---|---|
| 4,328,813 A | 5/1982 | Ray | |
| 5,000,177 A * | 3/1991 | Hoffmann et al. | 607/2 |
| 5,331,966 A | 7/1994 | Bennett et al. | |
| 5,476,496 A | 12/1995 | Strandberg et al. | |
| 5,927,277 A * | 7/1999 | Baudino et al. | 600/386 |
| 6,233,488 B1 * | 5/2001 | Hess | 607/58 |
| 6,253,109 B1 | 6/2001 | Gielen | |
| 6,427,086 B1 | 7/2002 | Fischell et al. | |
| 6,859,667 B2 | 2/2005 | Goode | |
| 2002/0091419 A1 * | 7/2002 | Firlik et al. | 607/45 |
| 2002/0116042 A1 | 8/2002 | Boling | |
| 2004/0186542 A1 | 9/2004 | Van Venrooij et al. | |

FOREIGN PATENT DOCUMENTS

| | | |
|---|---|---|
| EP | 0 033 242 | 8/1981 |
| WO | WO/00/57778 | 10/2000 |

OTHER PUBLICATIONS

Medtronics User's Manual for the Medtronic® Model 6983 Permanent Directional Indifferent Lead (Sep. 1977).
International Search Report for PCT/US2006/012148, mailed Sep. 29, 2006.

* cited by examiner

*Primary Examiner*—Carl H. Layno
*Assistant Examiner*—Yun Haeng Lee
(74) *Attorney, Agent, or Firm*—John W. Albrecht

(57) ABSTRACT

An assembly for sensing physiologic signals and delivering monopolar stimulation therapy includes a pulse generator, a lead body that is coupled to the pulse generator and includes a first lead, at least one stimulating electrode coupled to the first lead and adapted to receive stimulating pulses from the pulse generator, and a remote electrode that is coupled to the pulse generator and positioned away from the pulse generator.

9 Claims, 7 Drawing Sheets

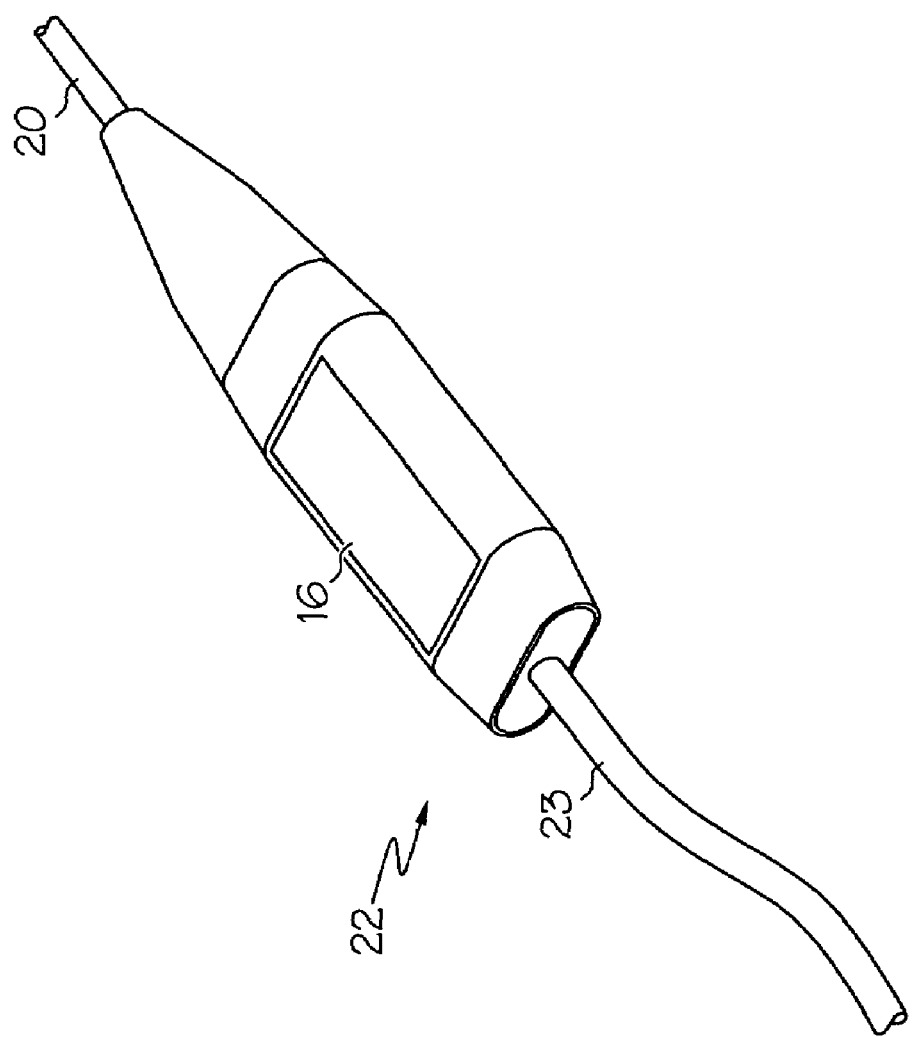

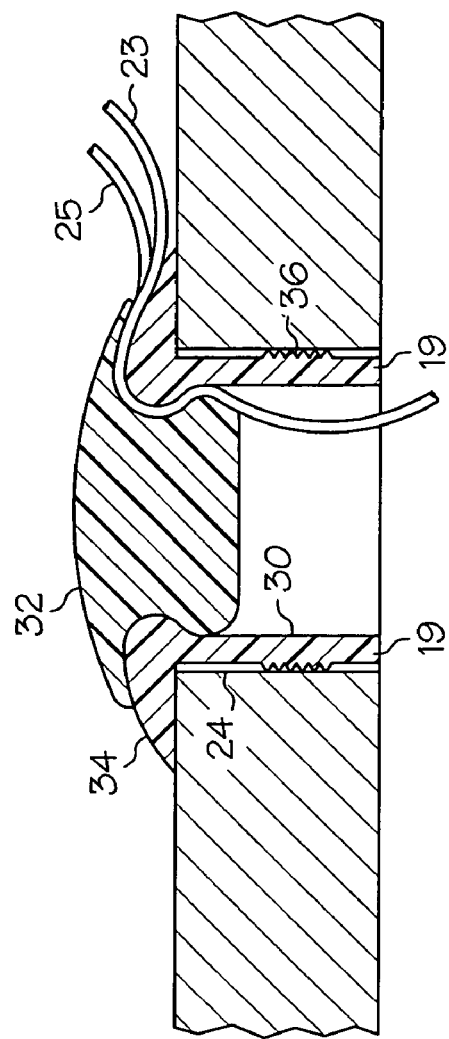
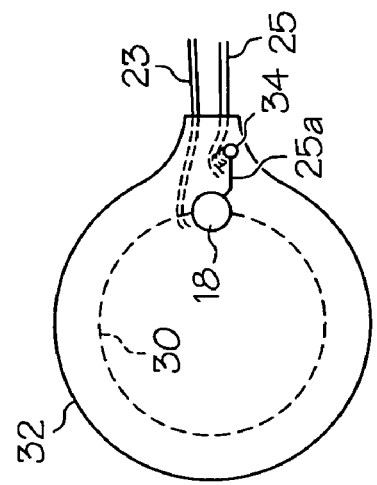

MONOPOLAR STIMULATION ASSEMBLY INCLUDING AT LEAST ONE REMOTE ELECTRODE

TECHNICAL FIELD

The present invention generally relates to various methods and apparatus for sensing physiologic signals and performing monopolar stimulation of body tissue, and more particularly relates to associated lead assemblies and methods of using the same.

BACKGROUND

Nervous system disorders affect millions of people, sometimes causing death and a degradation of life. Central and peripheral nervous system disorders include epilepsy, Parkinson's disease, essential tremor, dystonia, and multiple sclerosis (MS). Other nervous system disorders include mental health and psychiatric disorders, which also affect millions of individuals and include anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia.

Epilepsy is the most prevalent serious neurological disease across all ages. Epilepsy is a group of neurological conditions in which a person has or is predisposed to recurrent seizures. A seizure is a clinical manifestation of neurological activity indicative of a nervous system disorder, and results from excessive, hypersynchronous, abnormal electrical or neuronal activity in the brain. This electrical excitability of the brain may be likened to an intermittent electrical overload that manifests with sudden, recurrent, and transient changes of mental function, sensations, perceptions, and/or involuntary body movement. Because seizures are unpredictable, epilepsy affects a person's employability, psychosocial life, and ability to perform otherwise standard tasks such as operating vehicles or heavy equipment.

Treatment therapies for epilepsy and other nervous system disorders can include any number of possible modalities alone or in combination including, for example, electrical stimulation, magnetic stimulation, drug infusion, and/or brain temperature control. Each of these treatment modalities can be operated using closed-loop feedback control. An exemplary closed-loop feedback control technique includes receiving from a monitoring element a neurological signal that carries information about a symptom, a condition, or a nervous system disorder. The neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and peripheral nerve signals (cuff electrodes on a peripheral nerve). Monitoring elements include, for example, recording electrodes or various types of sensors.

Standard diagnostic EEG sensing requires two electrodes in contact with body tissue. The first electrode is placed near the desired source of the electrical activity that the physician desires to monitor, and is referred to as active. The second electrode, referred to as the reference, is typically placed outside of the cranium away from the desired source of electrical activity. For example, the reference electrode may be attached to the ear or mastoid, or at the back of the head. Such locations are considered "inactive" since sensing from these areas produces a potential that is close to zero. In a monitoring system or device, differential amplifiers measure the voltage difference between the reference electrode and other active electrodes located within the brain. The resulting intracranial signals are amplified and displayed as channels of EEG activity.

For implantable devices that perform EEG sensing, it is desirable to have the reference electrode contained within the body. The reference electrode is carefully positioned such that ECG and movement artifacts are not present in the measured signals. Also, if the signals are to be used for seizure detection, it is desirable that the reference electrode be remote from the seizure focus. The active electrodes are positioned either in direct or indirect contact with brain structures affecting a neurological condition for which sensing is being performed. For example, to treat epilepsy the active electrodes may be implanted in brain tissue at or near the seizure focus where they can sense EEG signals, detect a seizure event, and provide stimulation therapy. Conversely, the active electrodes may be positioned in an anatomical target distant from the seizure focus, but which is connected to the seizure focus by way of neuronal pathway projections. Activating pathway projections with electrical stimulation from a distant site (i.e., thalamus) may influence seizure activity at the focus (i.e., hippocampus/amygdala). With either approach, it is desirable to have a single electrode positioned away from the active electrodes, which can function as a reference for EEG sensing and/or function as an indifferent electrode for monopolar stimulation.

As previously alluded to, some devices that incorporate a feedback loop for sensing EEG signals also perform monopolar or bipolar tissue stimulation. Monopolar stimulation devices typically employ an implantable pulse generator, and a single lead having one or more active electrodes and a separate indifferent electrode. The active electrodes serve as the negative pole, and are normally disposed near the lead distal end. An indifferent electrode is frequently located on the exterior of the implantable pulse generator housing, which functions as the anode or positive pole. Electrical impulses occur as current flows between the active electrode and the indifferent electrode through the body tissue. Monopolar stimulation produces a radial current diffusion that covers an approximately spherical space around the active electrode.

In contrast to monopolar stimulation systems, bipolar stimulation systems utilize one or more electrodes as the positive pole, and one or more of the remaining electrodes act as the negative pole. The pulse generator housing is not used as an indifferent electrode. Usually, two adjacent or nearby electrodes are activated and respectively function as positive and negative poles. Bipolar stimulation creates a narrower and more focused current field than monopolar stimulation. However, monopolar stimulation is more frequently used because it usually requires lower stimulation parameters than bipolar stimulation to achieve the same clinical effect.

Despite the simplicity and effectiveness provided by a monopolar stimulation assembly, recent improvements in technology have created some situations in which the conventional coupling of the indifferent electrode to the implantable pulse generator housing is somewhat problematic. For instance, sometimes the implantable pulse generator can not function as a site for an indifferent electrode because the pulse generator already supports an electrode that is used for other functions such as recording electrocardiogram signals. In other cases, the pulse generator housing is made of a nonconductive material and can not support or function as an indifferent electrode. Also, in unusual circumstances patients have experienced sensations at the implantable pulse generator pocket during stimulation, perhaps attributable to the indifferent electrode.

Accordingly, it is desirable to provide systems and methods for performing EEG sensing and/or monopolar stimulation that overcome potential difficulties associated with implantable pulse generator size and function, and also reduce the potential for patient discomfort. In addition, it is desirable to provide methods and systems that can be adapted to accommodate a wide variety of implantable pulse generators, and to further accommodate the various methods for implanting and configuring such devices. Furthermore, other desirable features and characteristics of the present invention will become apparent from the subsequent detailed description and the appended claims, taken in conjunction with the accompanying drawings and the foregoing technical field and background.

BRIEF SUMMARY

An assembly is provided for referential sensing and delivering monopolar stimulation therapy. The assembly includes a pulse generator, a lead body that is coupled to the pulse generator and includes a first lead, at least one stimulating electrode coupled to the first lead and adapted to receive stimulating pulses from the pulse generator, and a remote electrode that is coupled to the pulse generator and positioned away from the pulse generator.

A monopolar stimulation apparatus is also provided for delivering therapeutic pulses to a targeted body tissue using at least one stimulating electrode coupled to a lead body. The apparatus includes a pulse generator, a header block adapted to couple the pulse generator to the lead body, and a remote electrode that is coupled to the pulse generator and positioned on the header block.

A monopolar stimulation assembly is also provided for delivering therapeutic pulses to targeted brain tissue using at least one stimulating electrode coupled to a lead body. The assembly includes a pulse generator, a lead body coupled to the pulse generator, a burr ring that defines an aperture and is adapted to be secured inside a cranium burr hole, a cap that is adapted to engage the burr ring and thereby close off the aperture, and a remote electrode that is coupled to the lead body and secured to the cap.

BRIEF DESCRIPTION OF THE DRAWINGS

The present invention will hereinafter be described in conjunction with the following drawing figures, wherein like numerals denote like elements.

FIG. 5 is a perspective view of an extension connector that is coupled to an intracranial lead and a lead extension;

FIG. 7 is a top view of a cap, having a reference electrode attached thereto, that is part of a ring and cap assembly; and FIG. 8 is a cross sectional view of a ring and cap assembly securing two intracranial leads and closing off a burr hole in a patient's cranium.

DETAILED DESCRIPTION

The following detailed description is merely exemplary in nature and is not intended to limit the invention or the application and uses of the invention. Furthermore, there is no intention to be bound by any expressed or implied theory presented in the preceding technical field, background, brief summary or the following detailed description.

One aspect of the present invention includes a monopolar stimulation assembly that includes an electrode that is removed from an implantable pulse generator, and thereby overcomes difficulties associated with attaching electrodes to implantable pulse generators having unaccommodating sizes, materials, or functions. The electrode can function as an indifferent electrode for monopolar stimulation and/or as a reference electrode for sensing electrical activity. Another aspect of the invention includes adapting the monopolar stimulation assemblies by placing the electrode at various positions between the implantable pulse generator and a body tissue being targeted for therapy.

Figure 1:
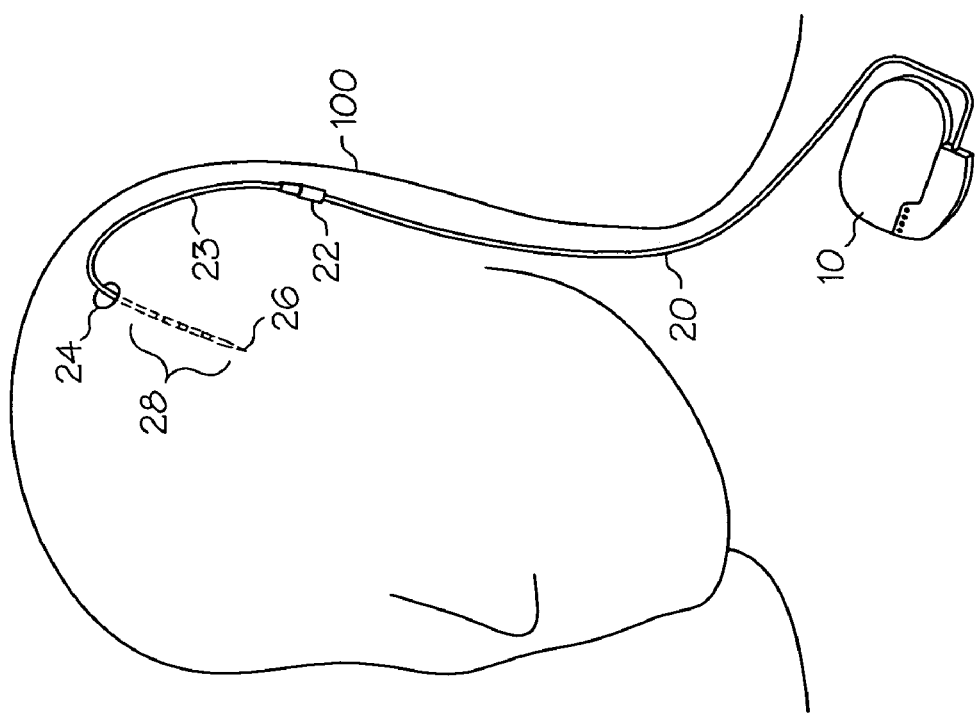
FIG. 1 is an illustration of an implantable monopolar stimulation assembly with reference to a patient for whom brain stimulation is enabled using the assembly.

Each of the monopolar stimulation assemblies described hereafter produces electrical impulses as a fully implantable system. Electrical impulses occur as current flows between an active electrode and an indifferent electrode through the body tissue. FIG. 1 illustrates the positions of the various monopolar stimulation assembly components when such components are implanted within a patient 100. The assembly depicted in FIG. 1 is a deep brain EEG sensing and stimulation system for the detection and termination of epileptic seizures, although this is only one exemplary brain stimulation system for which the features of the present invention may be utilized.

An implantable pulse generator (IPG) 10 is implanted proximate to the patient's clavicle. The IPG 10 includes a pulse generating source that is coupled to, and in some cases controlled by, EEG sensing circuitry. A lead extension 20 has a proximal end that is coupled to the pulse generating source in the IPG 10, and a distal end that is coupled to an extension connector 22, which is typically implanted near the patient's cranium. The extension connector 22 connects the lead extension 20 to an intracranial lead 23 in a manner that enables a physician to detach the intracranial lead 23 from the lead extension 20, and thereby remove or adjust the IPG 10 without disrupting the intracranial lead position about the patient's brain. One or more deep brain stimulation electrodes 28 are positioned near the intracranial lead distal end 26, and are inserted into targeted brain tissue. The lead extension 20, connector 22, and lead 23 usually extend from the IPG 10 between the dermis and the cranium. The electrodes 28 are positioned into or near the targeted brain tissue by passing some or all of the intracranial lead distal end 26 through a burr hole 24 surgically bored through the cranium.

Figure 2:
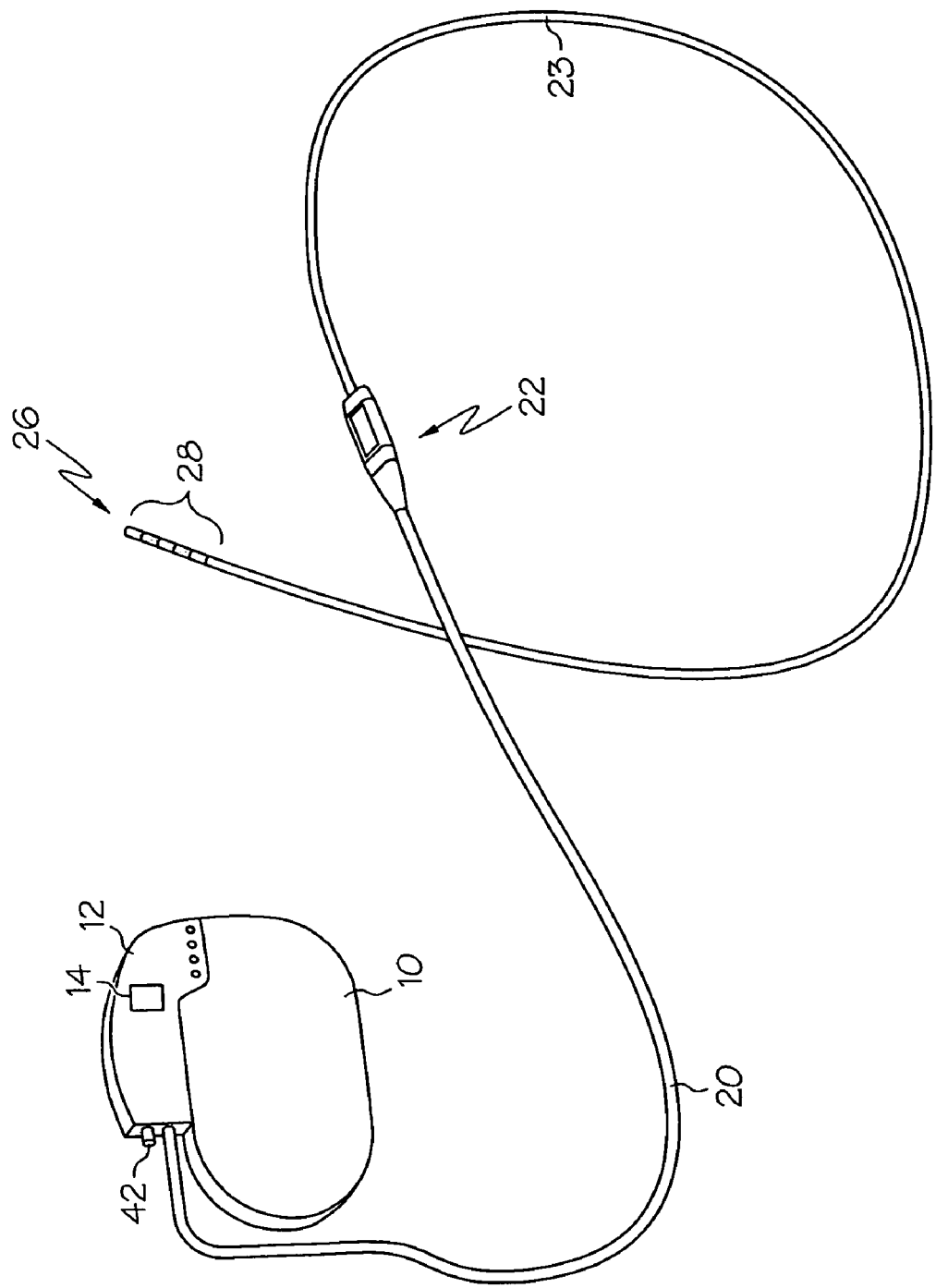
FIG. 2 is a detailed view of the monopolar stimulation assembly illustrated in FIG. 1.

FIG. 2 illustrates the same assembly from FIG. 1 in greater detail and outside the body. A header block 12 for the pulse generator couples the IPG 10 to the lead extension 20. As previously discussed, an indifferent electrode is typically located on the exterior of the implantable pulse generator housing, which serves as the positive pole and is coupled to the EEG sensing circuitry. As mentioned previously, there are some situations in which it is difficult or problematic to position the reference electrode directly on the IPG 10. One aspect of the inventive monopolar stimulation assembly includes positioning the indifferent electrode away from the IPG 10 and in remote locations with respect to the electrodes 28. For this reason, the indifferent electrode will hereafter be referred to as a remote electrode. Various positions and functions for the remote electrode will be subsequently described in detail.

Figure 3:
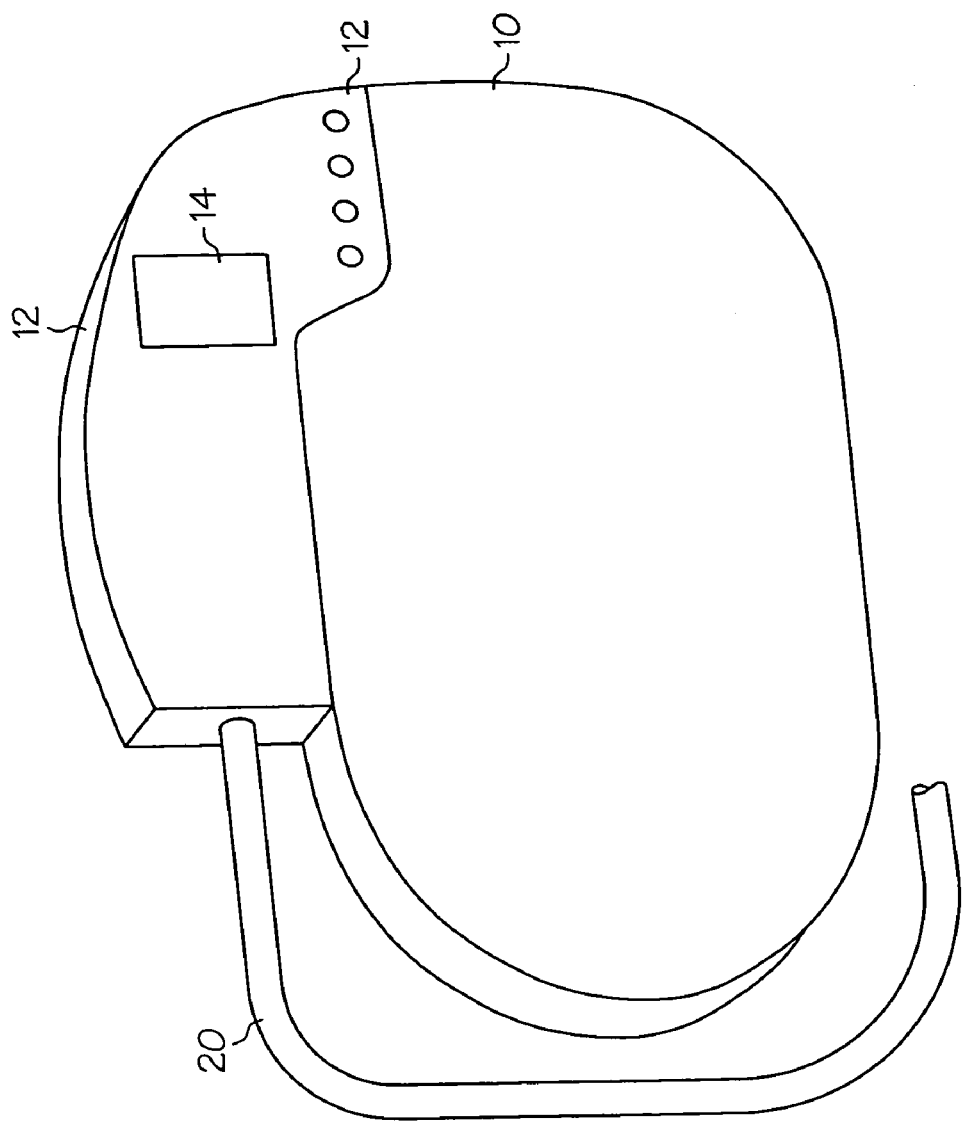
FIG. 3 is a perspective view of an implantable medical device coupled to a lead extension using an implantable pulse generator header that has a remote electrode positioned thereon.

FIG. 3 is a perspective view of the IPG 10 coupled to the lead extension 20 using an IPG header block 12. According to this embodiment, the remote electrode 14 is positioned on the header block 12 instead of the IPG 10. Electrical impulses occur as current flows through the body tissue between the one or more electrodes 28 on the intracranial lead 23 and the remote electrode 14. In this and other embodiments, the remote electrode 14 is adapted to function in various capacities, including as a reference electrode for sensing electrical signals including EEG signals, and as an indifferent electrode during monopolar stimulation.

Although not necessarily shown to scale in the figures, the remote electrode 14 is much larger than the one or more electrodes 28 on the intracranial lead 23. An exemplary remote electrode 14 is at least five times larger than the individual stimulating electrodes 28, and is preferably at least ten times larger than the individual stimulating electrodes 28.

Figure 4:
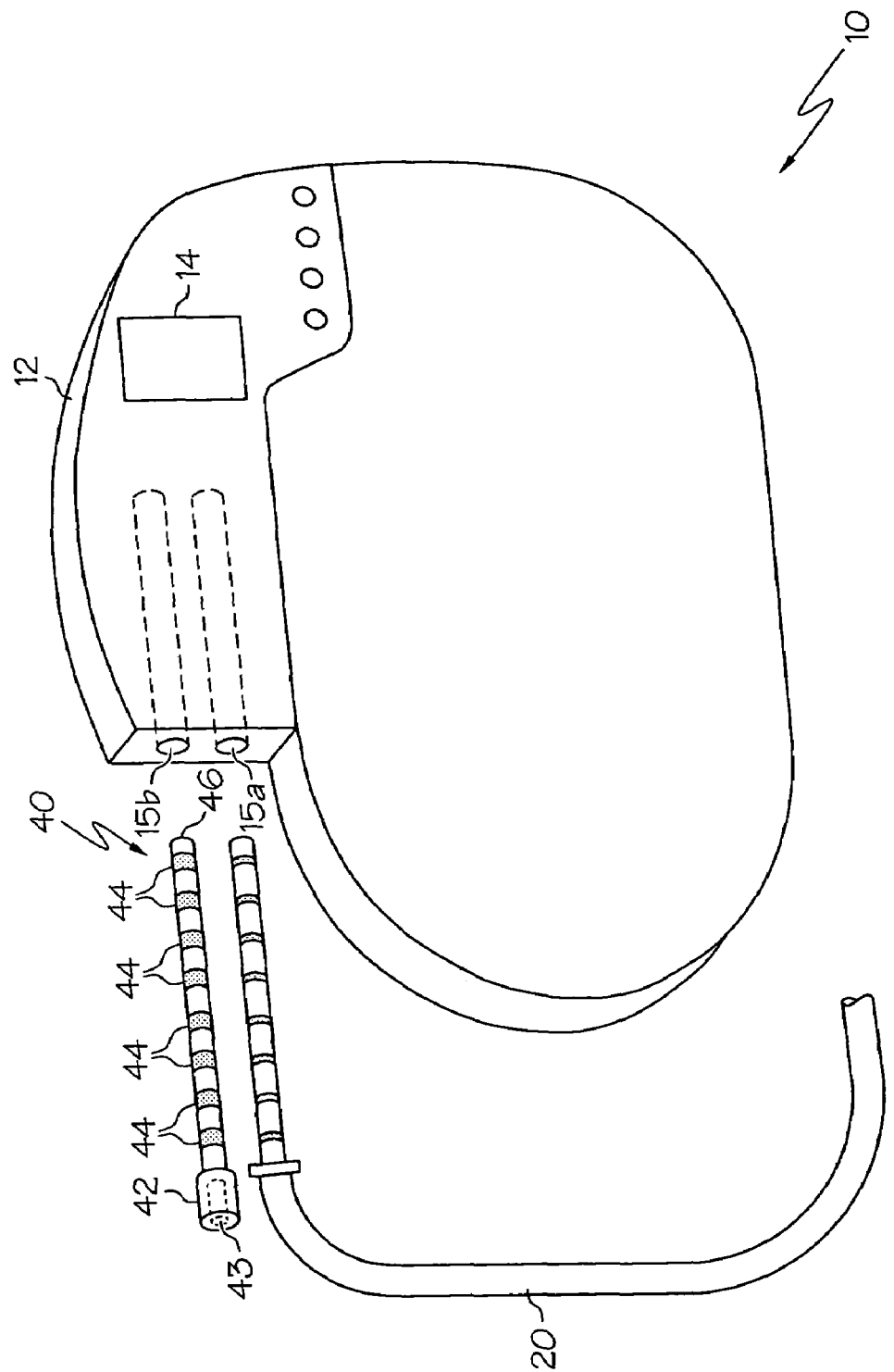
FIG. 4 is a perspective view of an implantable medical device, with a lead extension insertable into an implantable pulse generator header block, and a plug that has a first end that is also insertable into the header block and a second end that includes a remote electrode.

FIG. 4 illustrates the IPG 10, along with that header block 12 that is equipped with ports 15*a*, 15*b* that are adapted to receive proximal ends of the lead extension 20, and a plug 40 that includes an exemplary remote electrode 42. The plug 40 includes an extension 46 that is insertable into the header block port 15*a*. When inserted, the plug 40 is secured using a set-screw locking mechanism or other suitable locking means. A PTFE ring, a silicone seal, or other type of seal is used as necessary to expose the remote electrode 42 to body fluids while protecting the header block interior. FIG. 2 illustrates the remote electrode 42 exposed to the header block exterior environment when the plug 40 is inserted into the header block 12. Although the embodiment illustrated in FIGS. 2 and 4 includes both remote electrodes 14, 42 on the header block 12, the header block 12 can be equipped with just the remote electrode 14 as illustrated in FIG. 3, or with just the plug 40 that includes the remote electrode 42.

The plug 40 may be equipped with a port 43 that is adapted to be coupled to a second lead body that has a proximal end that is insertable into the port 43, and a distal end that includes active electrodes. The second lead body may include an extension similar to lead extension 20 and a connector similar to connector 22 that couples the lead extension to a lead equipped with active electrodes. Configured this way, the plug 40 includes a plurality of contacts 44. One of the contacts 44 receives electrical signals from the remote electrode 42, and one of the remaining contacts 44 receives electrical signals from the active electrodes from the second lead body. Contacts in the header block 12 match with the plug contacts 44 and electrically couple the remote electrode 42 and active electrodes on the second lead body, if any, to the IPG 10. In an exemplary embodiment, the contacts 44 are wired in parallel with respect to the remote electrode 42. However, according to the desired programming scheme and related circuitry considerations, it may be advantageous to use either a single channel or multiple channels in sequence.

The plug and remote electrode combination illustrated in FIGS. 2 and 4, as well as other remote electrode configurations described herein, is particularly useful to adapt some rechargeable IPG systems for monopolar stimulation. Although conventional monopolar stimulation assemblies utilize a conductive area of the IPG housing as a remote electrode, a conventional rechargeable IPG receives external RF energy to recharge, and the IPG housing is made from ceramic or other nonconductive materials. Consequently, conventional rechargeable IPG systems are typically used for bipolar stimulation. The plug 40 illustrated in FIG. 4 includes eight contacts 44 and enables adaptation of a modified extension from the header block to be used for monopolar stimulation since the large surface area remote electrode 42 is positioned on the header block 12 instead of on the IPG housing.

FIG. 5 is a perspective view of the extension connector 22 coupled to the intracranial lead 23 and the lead extension 20. According to this embodiment, a remote electrode 16 is positioned on the extension connector 22. In addition to transferring stimulation pulses toward the stimulating electrodes 28, the lead extension 20 provides an electrical connection from the remote electrode 16 back to the EEG sensing circuitry, or other circuitry coupled to the pulse generating circuitry, within the IPG 10. In another embodiment, remote electrodes are positioned on both the extension connector 22 and the IPG header 12 to provide more remote electrode surface area. Having remote electrodes positioned at both locations also creates lower impedance during a monopolar stimulation procedure.

Figure 6B:
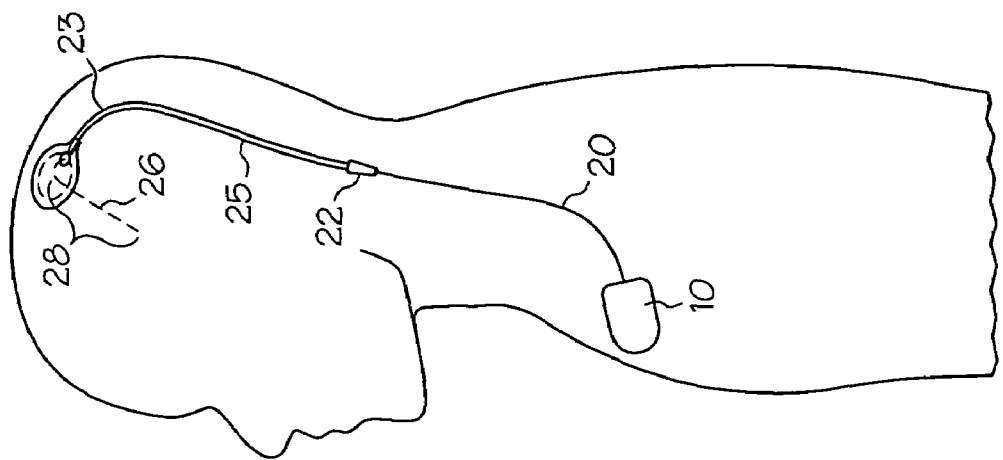
FIG. 6b is a top view of the patient to illustrate the position of the assembly electrodes with reference to the patient's cranium.
Figure 6A:
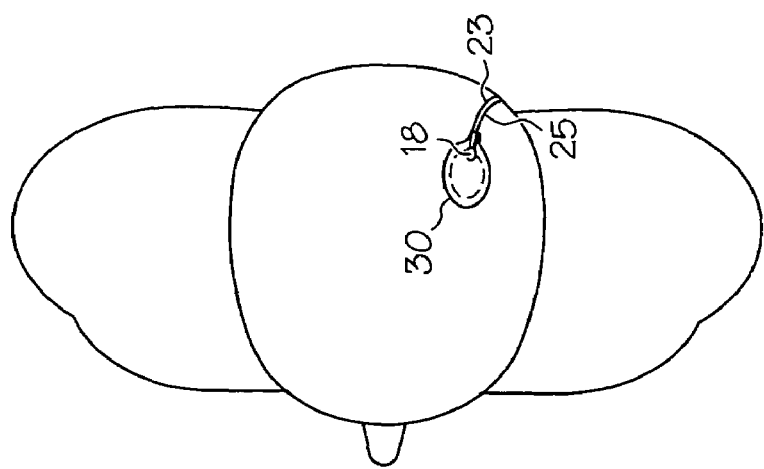
FIG. 6a is an illustration of another exemplary implantable monopolar stimulation assembly with reference to a patient for whom brain stimulation is enabled using the assembly.

Additional exemplary embodiments are illustrated in FIGS. 6 and 7, each of which illustrates another exemplary implantable monopolar stimulation assembly with reference to a patient. As in previously-described embodiments, the lead extension 20 has a proximal end that is coupled to the pulse generating source in the IPG 10, and a distal end that is coupled to the extension connector 22. In this embodiment, the extension connector 22 is bifurcated to connect the lead extension to two intracranial leads 23, 25. The first intracranial lead 23 includes one or more deep brain stimulation electrodes that are positioned near the intracranial lead distal end 26, and are inserted into or proximate targeted brain tissue by passing some or all of the intracranial lead distal end 26 through the burr hole 24 surgically bored through the cranium. The second intracranial lead 25 includes a remote electrode 18 that is positioned on or adjacent to the brain tissue.

As can be appreciated, once the electrodes 18, 28 are inserted or otherwise positioned about the brain, it is important that the electrodes 18, 28 and adjacent leads 23, 25 be secured in place. Even very slight movement of the electrodes can cause unsatisfactory results, and it is desirable to avoid repeated surgery to reposition them. There are several ways to position the electrodes 18, 28 on or adjacent to the brain tissue, and one effective securing assembly is the ring and cap combination illustrated in FIGS. 6 to 8.

FIG. 8 is a detailed cross sectional view of a ring 30 and a cap 32, together securing the two intracranial leads 23, 25 while also closing off a burr hole 24. The ring 30 includes an upper flange 34, circumferential ribs 36, and an aperture 38. The circumferential ribs 36 are positioned below the flange 34 along the periphery of the burr ring outer wall to engage with an outer side wall of the burr hole 24 and thereby assist in securing the ring 30 in place. A non-illustrated septum, which is formed from a penetrable material such as a biocompatible rubber or another solid elastomer, may be placed in the aperture 38, after the ring and leads 23, 25 are positioned about the patient's brain, to thereby close off the aperture 38. Lead 23 is inserted into the cranial cavity through the ring 30, after which the lead portion protruding from the ring 30 may be bent to the side. The cap 32 is then installed to engage the burr ring 30, and thereby further close off the aperture 38 and cover at least part of the upper flange portion 34.

As mentioned previously, the ring and cap combination is just one of several assemblies that can be used to secure the electrodes 18, 28. Likewise, there are several exemplary ways to use the ring 30 and cap 32 to position a remote electrode on or near the brain. For example, in the arrangement illustrated in FIG. 7 a remote electrode 18 is attached to, or imbedded into the cap 32. A wire 25a or other conductive element attaches the remote electrode 18 to a set screw 38 that is threaded into the cap 32. The set screw 38 is just one exemplary device that functions to secure the intracranial lead 25, and also to establish an electrical connection between the remote electrode 18 and the intracranial lead 25, which is in turn coupled to the IPG 10.

FIG. 8 illustrates another way to use the ring 30 and cap 32 to position a remote electrode on or near the brain. In this embodiment, the ring 30 extends entirely through the burr hole 24, and the lower edge of the ring that is closest to the dura mater covering the brain functions as a remote electrode 19.

In many of the embodiments described above, the monopolar stimulation assembly includes a remote electrode that is removed from an implantable pulse generator, and thereby overcomes difficulties associated with attaching electrodes to implantable pulse generators having small or unaccommodating sizes or functions. In many of the provided examples the remote electrode is a relatively large plate. In such cases, for example, the remote electrode can be used as a reference electrode to sense neurological activity. In an exemplary embodiment the reference electrode is used to sense brain activity for epilepsy, and must be distanced from a seizure focus. In another exemplary embodiment the remote electrode is used as a default reference location for spinal cord stimulation applications. Although the remote electrode is primarily described as relatively large in the preceding specification, the remote electrode can also be a relatively small sensing electrode.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing the exemplary embodiment or exemplary embodiments. It should be understood that various changes can be made in the function and arrangement of elements without departing from the scope of the invention as set forth in the appended claims and the legal equivalents thereof.

What is claimed is:

1. An assembly for treating neurological disorders by delivering therapeutic pulses to a targeted tissue of a patient's body, the apparatus comprising:
    a pulse generator adapted to be implanted in the patient's body at a location that is remote from the patient's cranium;
    a header block coupled to the pulse generator;
    a lead body comprising first and second leads, each of said first and second leads having a proximal end coupled to the header block and further having a distal end;
    at least one stimulating electrode coupled to the first lead distal end and adapted to receive stimulating pulses from the pulse generator and deliver the pulses to the targeted body tissue;
    a ring and cap assembly that includes
        a burr ring, defining an aperture and adapted to be secured inside a cranium burr hole and to permit insertion of the first lead through the aperture and into the targeted tissue, and
        a cap, adapted to engage the burr ring and thereby close off the aperture and to secure the first lead; and
    a remote electrode that is remotely located with respect to the at least one stimulating electrode and thereby adapted to be remotely located with respect to the targeted tissue, coupled to the second lead distal end and joined with the ring and cap assembly.

2. The assembly according to claim 1, wherein the remote electrode is imbedded into the cap.

3. The assembly according to claim 1, wherein the burr ring includes a lower edge adapted to be positioned inside the cranium burr hole, and the remote electrode is coupled to the burr ring lower edge.

4. The assembly according to claim 1, wherein the pulse generator includes sensing circuitry adapted to receive and process electrical signals from the targeted body tissue, and the remote electrode is a reference electrode adapted to sense the electrical signals.

5. The assembly according to claim 1, wherein the apparatus is a monopolar stimulation assembly and the remote electrode is an indifferent electrode.

6. The assembly according to claim 1, wherein the remote electrode is at least five times larger than the at least one stimulating electrode.

7. The assembly according to claim 1, wherein the remote electrode is at least ten times larger than the at least one stimulating electrode.

8. The assembly according to claim 1, wherein the lead body further comprises:
    an extension connector adapted to detachably connect an intracranial lead of the first lead with lead extension of the first lead, wherein a distal end of the intracranial lead is positioned near the at least one stimulating electrode, and wherein a proximal end of the lead extension is coupled to the pulse generator.

9. The assembly according to claim 1, wherein the pulse generator comprises:
    a pulse generating source; and
    EEG sensing circuitry coupled to the pulse generating source and adapted to control the pulse generating source.

* * * * *